United States Patent [19]

Snedeker

[11] Patent Number: 4,664,106
[45] Date of Patent: May 12, 1987

[54] WOUND DRESSING

[75] Inventor: Marvin L. Snedeker, Wyoming, Mich.

[73] Assignee: Labeltape Meditect Inc., Grand Rapids, Mich.

[21] Appl. No.: 811,829

[22] Filed: Dec. 20, 1985

[51] Int. Cl.[4] ............................................. A61L 15/00
[52] U.S. Cl. .................................................. 128/156
[58] Field of Search ........................ 128/156; 604/304

[56] References Cited

U.S. PATENT DOCUMENTS

| 2,292,995 | 8/1942 | Greenwoll | 128/156 |
| 2,629,378 | 2/1953 | Barton | 128/268 |
| 2,681,732 | 6/1954 | Brady | 206/56 |
| 3,038,597 | 6/1962 | Brady, Jr. | 206/56 |
| 3,143,208 | 8/1964 | Sizemore, Jr. | 206/56 |
| 3,260,261 | 7/1966 | Gallovich | 128/149 |
| 3,315,387 | 4/1967 | Heuser | 40/2 |
| 3,550,589 | 12/1970 | Wallerstein | 128/156 |
| 3,616,114 | 10/1971 | Hamaguchi et al. | 161/39 |
| 3,645,835 | 2/1972 | Hodgson | 161/146 |
| 3,709,221 | 1/1973 | Riely | 128/156 |
| 4,122,552 | 10/1978 | Tedford | 2/78 R |
| 4,176,664 | 12/1979 | Kalish | 128/156 |
| 4,192,299 | 3/1980 | Sabatano | 128/155 |
| 4,219,596 | 8/1980 | Takemoto et al. | 428/41 |
| 4,265,234 | 5/1981 | Schaar | 128/156 |
| 4,281,650 | 8/1981 | Spiegelberg | 128/156 |
| 4,302,500 | 11/1981 | Flora | 428/284 |
| 4,341,208 | 7/1982 | Gordon | 128/156 |
| 4,367,252 | 1/1983 | Tordjman | 428/41 |
| 4,418,822 | 12/1983 | Dotta | 206/441 |
| 4,420,519 | 12/1983 | Slemmons | 428/40 |
| 4,460,370 | 7/1984 | Allison et al. | 604/897 |
| 4,485,809 | 12/1984 | Dellas | 128/156 |
| 4,513,739 | 4/1985 | Johns | 128/156 |

OTHER PUBLICATIONS 3M package publication and sample included.
Johnson & Johnson package publication and enclosed wound dressing.

Primary Examiner—Gregory E. McNeill
Attorney, Agent, or Firm—Price, Heneveld, Cooper, DeWitt & Litton

[57] ABSTRACT

The specification discloses a wound dressing or like applique including an adhesively coated upper layer backed by a release liner wherein the upper layer is perforated and the release liner is cut, there also being a slit extending through both the release liner and the upper layer from the peripheral edge of the article to the perforation and cut lines in the respective upper layer and release liner. This facilitates removal of the offal portion from that portion of the upper layer which is to be adhered to a wound or other surface.

10 Claims, 5 Drawing Figures

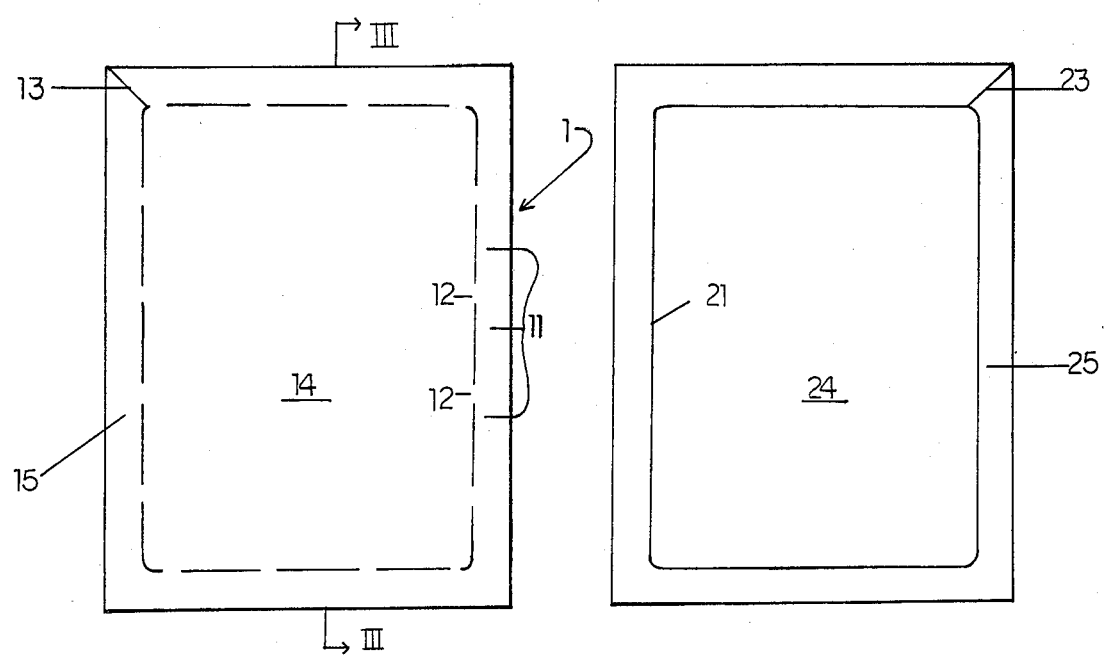
FIG. 1  FIG. 2
FIG. 3
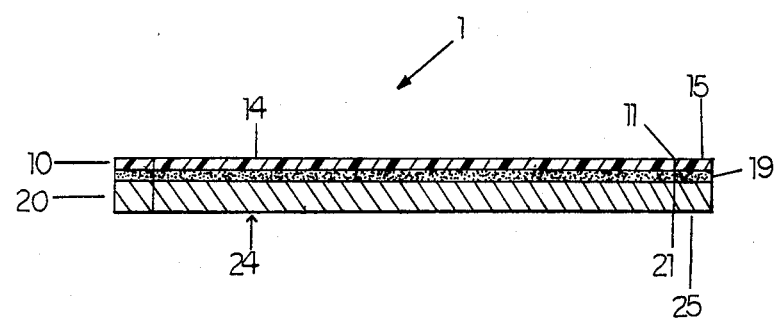

WOUND DRESSING

BACKGROUND OF THE INVENTION

The present invention relates to wound dressings or like appliques. Wound dressings comprising adhesively coated, thin polymeric films have become popular because they allow the wound to breathe. However, because they are thin, they are difficult to apply to the wound without wrinkling or sticking on themselves. Also, it is difficult to separate the wound dressing from its release liner.

Artisans have attempted to overcome this by cutting a perforation line in the polymeric film over a solid cut line in the release liner to thereby define a polymeric wound covering portion, a release liner covering only the wound covering portion, and offal comprising the perimeter portion of the film and the perimeter portion of the release liner. In use, one first peels away the center cut portion of the release liner, leaving the adhesive coating on the wound covering portion exposed. One then grips the offal portion on opposite ends to facilitate firm application of the wound covering portion to the wound area. The offal is then peeled away by tearing the film along the perforation line.

There are several problems with such bandages. First, it is difficult to separate the central portion of the release liner from the wound covering portion. There is a tendency to tear the polymeric film along its perforation line when the central portion of the release liner is removed. This is especially true if the perforation line is too weak, i.e., if the bridges between perforations are too short for a given thickness of polymeric film.

Alternatively, if the perforation line is too strong, it is difficult to tear the offal away from the wound covering portion of the film when it is adhered to the skin or other substrate. There is a tendency to lift the edge of the wound covering from the person's skin when one attempts to peel away the offal.

One attempt to obviate these drawbacks is disclosed in U.S. Pat. No. 4,485,809 to Dellas issued Dec. 4, 1984. Dellas offsets the cut line in the release liner outwardly from the perforation line in the polymeric film, theoretically making it easier to peel away the central portion of the release liner without simultaneously peeling away the wound covering portion of the polymer film. However, Dellas requires the use of two separate die cuts in order to manufacture his wound dressing. This makes it a more costly product.

SUMMARY OF THE INVENTION

The foregoing problems are all eliminated in the present invention by the provision of a slit through the release liner and the polymeric film, extending from the peripheral edge of the offal to the interior cut and perforated edges of the offal. By reason of this slit, the user can grasp the offal on one side of the slit and tear it generally laterally and upwardly away from the perforation line in the polymeric film, rather than being forced to lift the offal directly away from the surface to which the wound covering has been adhered. As a result, a stronger perforation line can be used in the polymeric film, since there is much less tendency to lift the wound covering portion of the film when one is stripping the offal with a combined lateral and upward motion.

These and other objects and advantages of the invention will be more fully understood and appreciated by reference to the written specification and appended drawings.

BRIEF DESCRIPTION OF THE DRAWINGS

FIG. 1 is top plane view of a wound dressing in accordance with the present invention;

FIG. 2 is a bottom plane view thereof;

FIG. 3 is a cross-sectional view taken along plane III—III of FIG. 1;

DESCRIPTION OF THE PREFERRED EMBODIMENT

Figure 4:
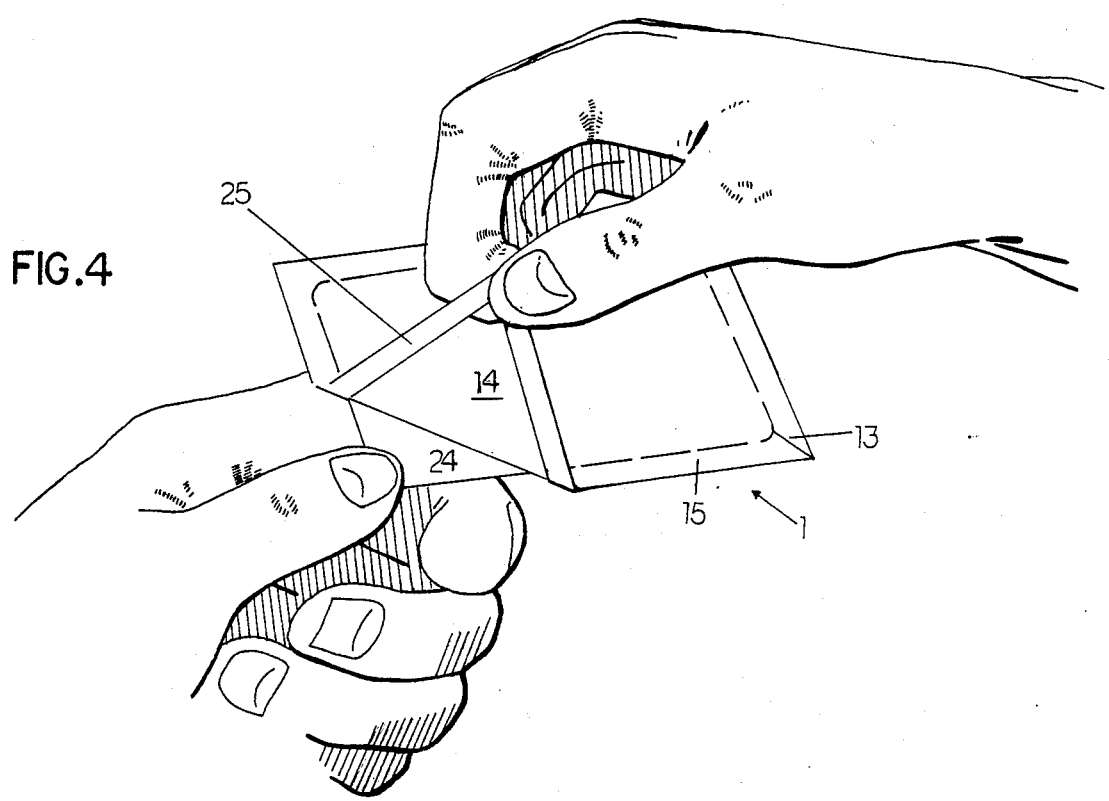
FIG. 4 is a perspective view showing a user peeling the central portion of the release liner away from the wound covering portion of the polymeric film.

In the preferred embodiment, wound covering 1 of the present invention comprises an upper layer of polymeric film material 10 having an adhesive surface 19 which, prior to use, is protected by a layer of release liner 20 (FIG. 3). Film 10 includes a perforation line 11 near its peripheral edge to define a wound covering portion 14 to the inside thereof and an offal portion 15 outside perforation line 11 (FIG. 1). Release liner 20 is cut with a complete cut line 21 which is in alignment with perforation line 11 to thereby define a wound covering portion 24 inside cut line 21 and an offal portion 25 outside of line 21 (FIG. 2). Both offal 15 of film 10 and offal 25 of release liner 20 are slit on a common line at 13 and 23 respectively (FIGS. 1 and 2). Slit 13, 23 is preferably located at a corner of wound covering 1.

Polymeric film 10 can be any of the various polymeric films used in breathable wound coverings. Polyurethene film is one commonly used material. Copolyester film is used. Such films typically have thicknesses of from about 0.0005 inches to about 0.0015 inches for purposes of use in wound coverings.

Perforation line 11 comprises individual perforations 11 with bridges of material 12 therebetween. The precise length of perforations 11 and the bridges of material 12 which extend between them can be arrived at empirically and will vary depending on the thickness of film 10 and the adhesiveness of the adhesive coating 19 thereon. If the adhesive holds better, perforation line 11 can be stronger. In the preferred embodiment, the perforations 11 have a length of from about $\frac{3}{8}$ to about $\frac{1}{2}$ inches and bridges 12 have a length of from about 0.015 to about 0.060 inches. Obviously, this varies with material used. A stronger, thicker film will require narrower bridges 12, while a thinner film of weaker material will require a wider bridge. For a polyurethane film having a thickness of 0.001 inch, it has been found that a perforation length of $\frac{1}{2}$ inch and a bridge length of 0.020 to 0.030 inches are desirable.

Corner slit 13 in film 10 extends from the perimeter of wound covering 1 to perforation line 11, except for a small bridge 13a generally at the middle thereof. Bridge 13a has generally the same dimension as bridges 12. It helps keep the ends of offal 15/25 under control until the user is ready to strip it away. Otherwise, it might have a tendency to begin tearing away on its own. Preferably, it joins with one of the perforations 11 rather than terminating at a bridge 12.

The precise width of the trim or offal portion 15 is not critical. It should be wide enough to make it easy for a user to grasp between his thumb and forefinger, but not so wide as to result in excessive waste of material. A width of from about ¼ to about ½ inch has been found satisfactory. Larger bandages would require wider margins, e.g., one inch.

The adhesive material applied to polymeric film 10 is a conventional wound covering adhesive. Many different materials are available to those skilled in the art, most having proprietary formulas. Acrylic adhesives are operable. Such adhesives are usually applied to a thickness of from about 0.001 to about 0.0025 inches. It is desirable that adhesive layer 19 be sufficiently thin that the wound can breathe through the adhesive material and through polymeric film 10.

Release liner 20 can be a conventional smooth surface paper material of the type typically used for release liners. Release liner 20 is sufficiently thick to give some body to wound covering 1 and make it easier to handle. Release liners typically have thickness of from about 0.004 to about 0.0075 inches. It is preferably cut along center cut line 21 in alignment with perforations 11 in film 10. In this way, a single die can be used to effect a single die cut simultaneously through release liner 20 and film 10.

Slit line 23 is similarly in alignment with slit line 13. Slit line 23 should extend from the peripheral edge of wound covering 1 to cut line 21.

In use, one first removes the center covering portion 24 of release liner 20 by simultaneously grasping a corner of the combined offal material 15 and 25 and a corner of central release liner portion 24 (FIG. 4). Central portion 24 is completely peeled away from the wound covering portion 14 of polymeric film 10. Perforation line 11 is sufficiently strong, due to the length of bridges 12 and the number thereof, that wound covering portion 14 does not readily separate from polymeric film 10 and peel away with central covering portion 24 of release liner 20.

Figure 5:
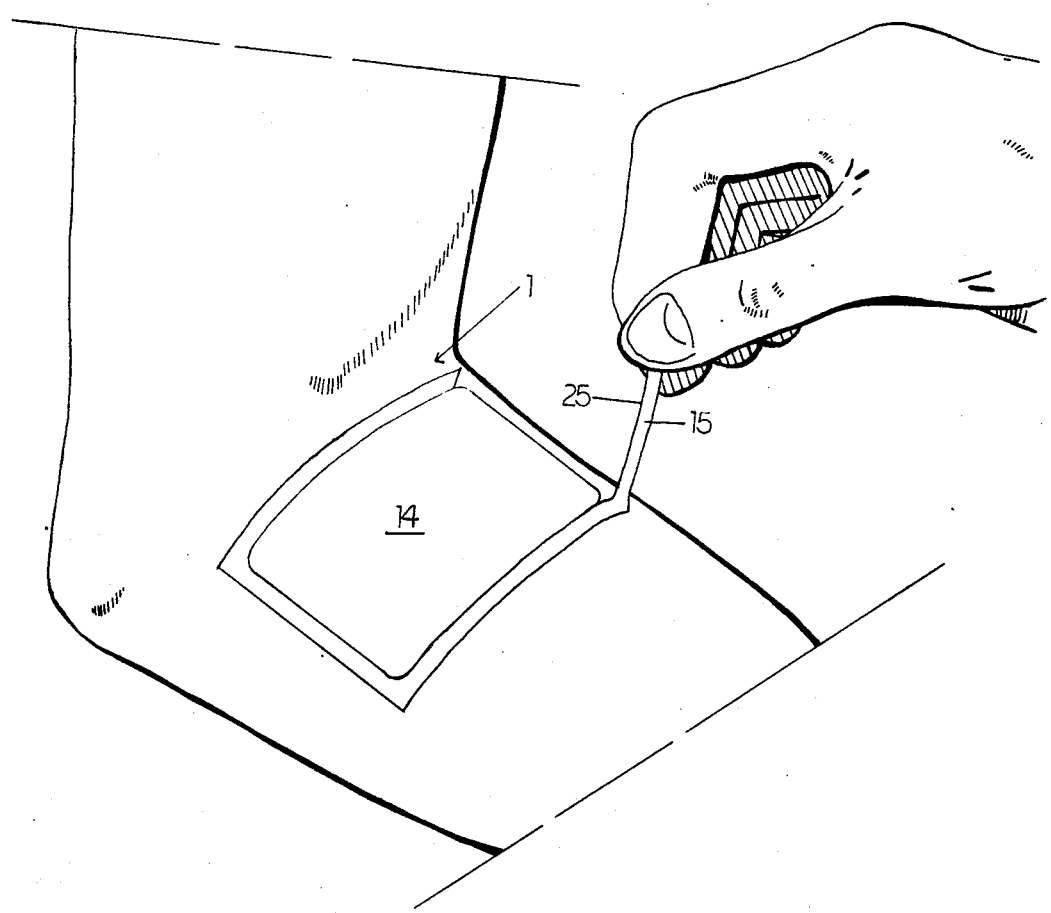
FIG. 5 is a perspective view showing the wound covering applied to a person's arm with user stripping the offal away from the wound covering portion of the polymeric film.

With release liner portion 24 removed, the user grasps covering 1 on either end or on either side and applies it to the wound, which is shown on an arm 2 in FIG. 5. Once wound covering portion 14 has been gently pressed against the surface to which it is to adhere, the user grasps offal 15/25 at a point adjacent slit line 13/23. The user then pulls offal 15/25 laterally and upwardly away from wound covering portion 14 of polymeric film 10 (FIG. 5). This motion is continued all the way around wound covering 14 until offal 15/25 is completely removed. Wound covering 14 is now firmly in place and there has been little tendency for its edges to be peeled away from the surface to which it has been applied. This minimizes weakening of the adhesive bond between covering 14 and the skin and also minimizes the chance for germs and the like to slip in underneath covering 14.

Of course, it is understood that the above is merely a preferred embodiment of this invention, and that various changes and alterations can be made without deviating from the spirit and broader aspects thereof.

The embodiments of the invention in which an exclusive property or privilege is claimed are defined as follows:

1. A wound covering or like applique including an adhesive coated upper layer and a release liner covering said adhesive, there being a perforation line in said upper layer to define a central portion which is to be applied to a surface and a generally comparable cut line in the release liner to define a central portion of release liner generally covering said central portion of said upper layer, the improvement comprising:

a slit in said upper layer extending from the periphery thereof to said perforation line and a slit in said release liner, in alignment with said slit in said upper layer, and extending from the periphery of said release liner to said cut line, whereby said central portion of said release liner can be peeled away from said central portion of said upper layer, said upper layer applied to the desired surface and said offal portions of said release liner and said upper layer readily peeled away by grasping said offal portions at a point generally adjacent said slit lines and pulling said offal portions away from said central portion of said upper layer to thereby break said perforation line.

2. The article of claim 1 in which said slit in said upper layer joins a perforation of said perforation line.

3. The article of claim 1 in which said slit in said upper layer is broken to define a bridge of film material at said breaks.

4. The article of claim 3 in which said upper layer comprises a relatively thin, polymeric film.

5. The article of claim 4 in which said polymeric film has a thickness of from about 0.0005 to about 0.0015 inches.

6. The article of claim 5 in which said perforation line comprises perforations having a length of from about ⅜ to about ½ inch with material bridges of from about 0.015 to about 0.060 inches between adjacent perforations.

7. The article of claim 1 in which said upper layer comprises a relatively thin, polymeric film.

8. The article of claim 6 in which said polymeric film has a thickness of from about 0.0005 to about 0.0015 inches.

9. The article of claim 7 in which said perforation line comprises perforations having a length of from about ⅜ to about ½ inch with material bridges of from about 0.015 to about 0.060 inches between adjacent perforations.

10. The article of claim 1 in which said slit in said upper layer is broken to define a bridge of film material at said breaks.

* * * * *